United States Patent [19]

Lindsay

[11] Patent Number: 5,616,137
[45] Date of Patent: Apr. 1, 1997

[54] LOW VELOCITY AORTIC CANNULA

[75] Inventor: Erin J. Lindsay, Dexter, Mich.

[73] Assignee: Minnesota Mining and Manufacturing Company, St. Paul, Minn.

[21] Appl. No.: 392,075

[22] Filed: Feb. 22, 1995

[51] Int. Cl.⁶ .................................................. A61M 5/00
[52] U.S. Cl. ............................................ 604/264; 604/53
[58] Field of Search ........................... 604/264, 53, 9, 604/7, 8, 19, 27, 30, 93, 247, 256, 280, 246

[56] References Cited

U.S. PATENT DOCUMENTS

| | | |
|---|---|---|
| 275,405 | 4/1883 | Parker . |
| 609,280 | 8/1898 | King . |
| 611,454 | 9/1898 | Longden . |
| 829,952 | 9/1906 | Dean . |
| 2,356,659 | 8/1944 | de Paiva Aguiar . |
| 2,393,728 | 1/1946 | de P. Aguiar . |
| 2,854,983 | 10/1958 | Baskin . |
| 2,862,498 | 12/1958 | Weekes . |
| 3,108,595 | 10/1963 | Overment . |
| 3,397,699 | 8/1968 | Kohl . |
| 3,568,659 | 3/1971 | Karnegis . |
| 3,605,750 | 9/1971 | Sheridan et al. . |
| 3,799,172 | 3/1974 | Szpur . |
| 3,938,530 | 2/1976 | Santomieri . |
| 3,955,573 | 5/1976 | Hansen et al. . |
| 3,964,484 | 6/1976 | Reynolds et al. . |
| 4,297,115 | 10/1981 | Johnson, Jr. . |
| 4,321,920 | 3/1982 | Gillig . |
| 4,375,816 | 3/1983 | Labianca . |
| 4,437,856 | 3/1984 | Valli . |
| 4,474,206 | 10/1984 | Cannon . |
| 4,522,195 | 6/1985 | Schiff . |
| 4,535,757 | 8/1985 | Webster, Jr. . |
| 4,575,371 | 3/1986 | Nordqvist et al. . |
| 4,580,568 | 4/1986 | Gianturco . |
| 4,596,548 | 6/1986 | DeVries et al. . |
| 4,617,019 | 10/1986 | Fecht et al. . |
| 4,643,712 | 2/1987 | Kulik et al. . |
| 4,655,745 | 4/1987 | Corbett . |
| 4,680,029 | 7/1987 | Ranford et al. . |
| 4,693,243 | 9/1987 | Buras . |
| 4,787,882 | 11/1988 | Claren . |
| 4,795,439 | 1/1989 | Guest . |
| 4,795,446 | 1/1989 | Fecht . |
| 4,801,297 | 1/1989 | Mueller . |
| 4,802,819 | 2/1989 | Bevington et al. . |
| 4,813,935 | 3/1989 | Haber et al. . |
| 4,863,441 | 9/1989 | Lindsay et al. . |
| 4,921,478 | 5/1990 | Solano et al. . |
| 4,966,585 | 10/1990 | Gangemi . |
| 5,021,044 | 6/1991 | Sharkawy . |
| 5,084,033 | 1/1992 | O'Neill et al. . |
| 5,147,332 | 9/1992 | Moorehead ............................ 604/247 |
| 5,300,022 | 4/1994 | Klapper et al. . |
| 5,354,288 | 10/1994 | Cosgrove et al. ...................... 604/264 |

OTHER PUBLICATIONS

Advertising flyer for "Argyle® Lighthouse Tip Vena Caval Catheter", by Sherwood Medical Company, dated 1985.
Charles C. Reed, Diane K. Clark, Chapter 19, "Cannulation", Chapter 23 Myocardial Protection, *Cardiopulmonary Perfusion*, Texas Medical Press, Inc., Houston, Texas, 1975.
"Atheroembolism From The Ascending Aorta", *The Journal of Thoracic and Cardiovascular Surgery*, C. Blauth et al., 1104–1111.

*Primary Examiner*—Corrine M. McDermott
*Assistant Examiner*—N. Kent Gring
*Attorney, Agent, or Firm*—Gary L. Griswold; Walter N. Kirn; Stephen W. Bauer

[57] ABSTRACT

An aortic cannula having a distal end adapted to be inserted into the aorta to deliver fluid to the aorta has a flexible tip with a plurality of helical slits that widen and narrow in response to the pressure in the cannula, widening in response to an increase in pressure to reduce exit velocity of the fluid.

21 Claims, 2 Drawing Sheets

5,616,137

LOW VELOCITY AORTIC CANNULA

This invention relates to a low velocity aortic cannula for use during heart surgery, and a method of delivering fluid to the aorta using a low velocity aortic cannula.

BACKGROUND AND SUMMARY OF THE INVENTION

Aortic cannulas are used to return blood or provide other fluid to the aorta while the heart is by-passed during heart surgery. These cannulas are purposely made with small diameters (typically six to eight millimeters, but even smaller for pediatric applications) to minimize the disruption to the aorta, which in many heart surgery patients have advanced complex atherosclerotic lesions with adherent blood thrombi. The flow velocities through these small diameter cannula must be very high in order to maintain a satisfactory blood flow rate of about five to seven liters per minute. In at least some styles of conventional aortic cannula now in use, this high velocity resulted in "jet" flow emanating from the distal end of the cannula, which acted as a nozzle. It is believed that the force of this narrow jet stream may dislodge atheromatous material and/or adherent thrombi from the walls of the aorta, causing embolisms. As surgical equipment and techniques improve, making heart surgery available to older and more seriously ill patients, thromboatheroembolisms affect an increasing number of patients due to the increasing extent of atherosclerosis with age.

The size of aortic cannula may be constrained by the constricted size of the aorta of the typical heart surgery patient. Moreover, the ability to diffuse flow is restricted by the fragility of the blood, which is easily damaged by the shear stresses associated with turbulence.

The aortic cannulas of the present invention are adapted to provide high volume flow at relatively lower exit flow velocities than the conventional aortic cannulas presently available, thereby reducing the jet flow and consequently reducing the incidence of thromboatheroembolisms. Generally aortic cannulas constructed according to the principles of this invention comprise a plurality of spiral or helical slits in the distal tip to form a plurality of outlet openings in the sidewall of cannula adjacent the distal end. The slits open and close in response to pressure in the cannula, preventing a high pressure build up, and thereby reducing jet flow from the cannula. The slots allow the flow to quickly establish a stable, more uniform velocity flow.

Thus, the aortic cannula of the present invention reduces the high velocity jetting that can occur with some conventional aortic cannulas, while maintaining flow rate and minimizing damage to the blood.

These and other features and advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figure 1:
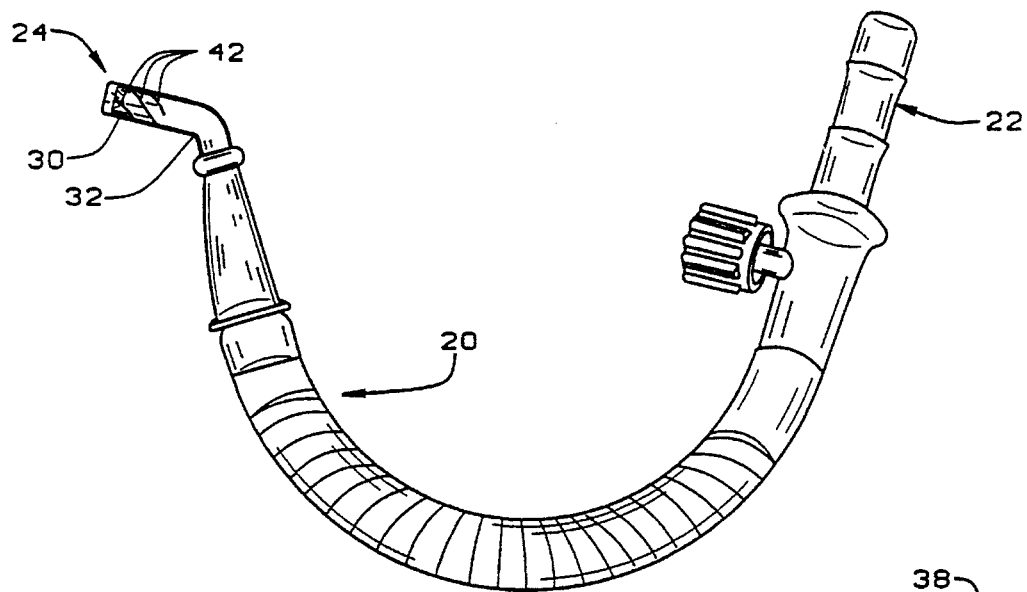
FIG. 1 is a side elevation view of a first embodiment of an aortic cannula constructed according to the principles of this invention.
Figure 2:
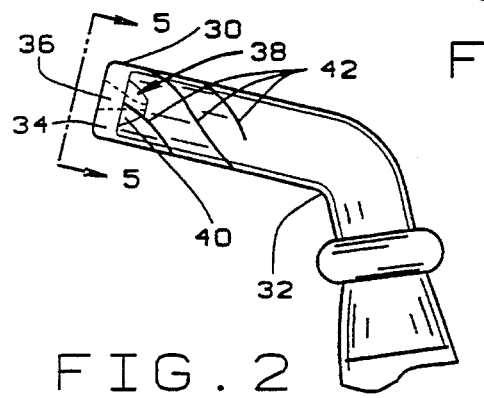
FIG. 2 is a left side elevation view of the tip of the first embodiment of the aortic cannula shown in FIG. 1.
Figure 3:
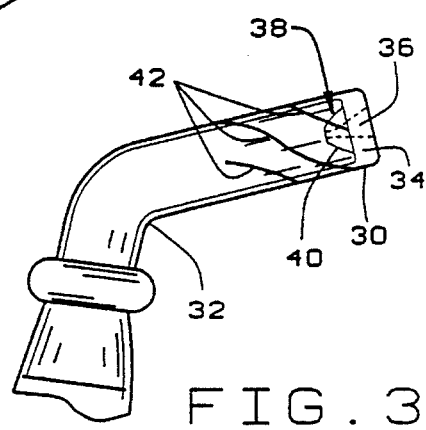
FIG. 3 is a right side elevation view of the tip of the first embodiment of the aortic cannula.
Figure 4:
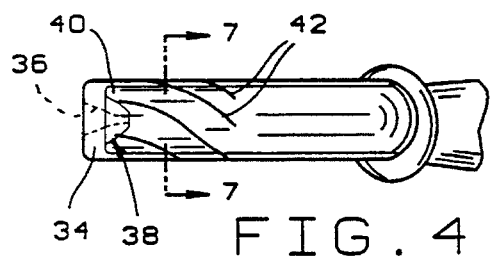
FIG. 4 is a top plan view of the tip of the first embodiment of the aortic cannula.
Figure 5:
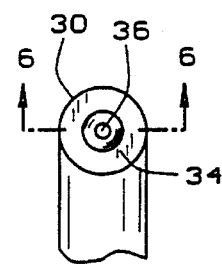
FIG. 5 is an end elevation view of the tip of the first embodiment of the aortic cannula.

A first embodiment of an aortic cannula constructed according to the principles of this invention is indicated generally as 20 in FIG. 1. The cannula has a proximal end 22 and a distal end 24, and a lumen 26 extending therebetween. There is a conventional tubing connector 28 at the proximal end of the cannula 20 for connecting the cannula to a blood supply circuit. The distal end of the cannula 20 has a tip 30 adapted to be inserted though a slit in the wall of an aorta to deliver blood or other fluid to the aorta, for example, during heart surgery. As shown in the Figures, the tip is bent at 32 to facilitate the introduction of the tip into the aorta, as well as to aid in retaining the tip in the aorta. However, the tip of the cannula could be straight, if desired.

Figure 6:
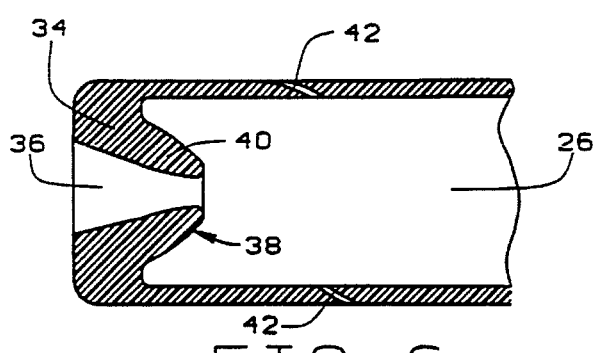
FIG. 6 is a longitudinal cross-sectional view of the tip of the first embodiment of the aortic cannula, taken along the plane of line 6—6 in FIG. 5.

As best shown in FIG. 6, the end of the tip 30 has an annular cap 34 thereon, with a central opening 36 there through. The cap 34 partially blocks the lumen 26, while the central opening 36 allows the passage of some fluid through distal end of the cannula. The opening 36 preferably has a frustoconical shape, widening in the distal direction. A diffuser 38, for example a cone 40, can be provided on the proximal side of cap 34. The cone 40 extends proximally inside the lumen 26, to gently diffuse at least a portion of the flow through the lumen radially outwardly.

The sidewall of the tip 30 is preferably made from a resilient, flexible material. The material is preferably a plastic having a durometer of between 50 and 80 Shore A. The sidewall of the tip has a plurality of helical or spiral slits 42 therein, defining a plurality of helical struts 44. As shown in the Figures, the helical slits extend clockwise, but the invention is not so limited, and the helical slits could extend counter-clockwise. The length of the slits 42 is preferably about one to one and one half times the diameter of the cannula. The distal ends of the slits 42 preferably extend to the base of the diffuser 38, so that there is no dead space distal of the distal ends of the slits 42, in which blood or fluid can accumulate. There are preferably between three and eight slits 42 in the sidewall.

Figure 7:
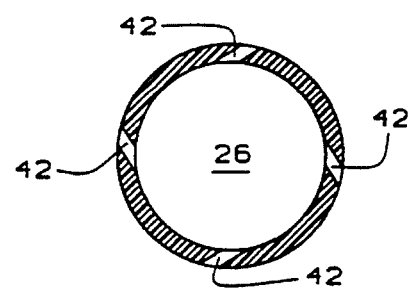
FIG. 7 is a transverse cross-sectional view of the tip of the first embodiment of the aortic cannula, taken along the plane of line 7—7 in FIG. 4.
Figure 8:
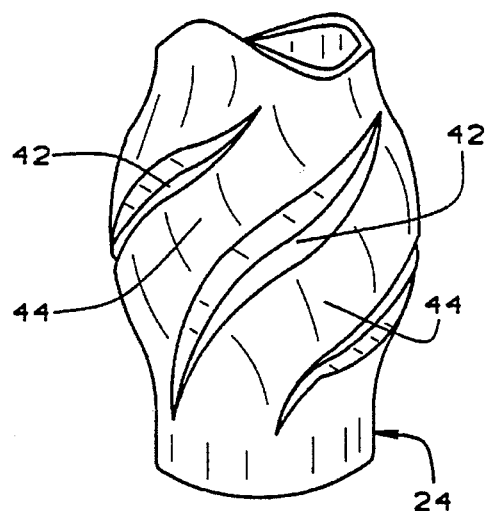
FIG. 8 is a side elevation view of the tip of the first embodiment of the aortic cannula, partially expanded.

As shown in FIG. 6, the slits 42 are preferably oriented at an angle with respect to the axial direction of the tip, extending outwardly and distally, thereby directing flow through the slits generally distally. As shown in FIG. 7, the slits 42 are preferably oriented at an angle with respect to the radial direction of the tip. The slits are preferably oriented at an angle of between 45° and 60° to the radial direction, in the opposite direction as the helical turn of the slits when viewed from the proximal end. Thus, for example where, as shown in the drawings, the slits turn in a clockwise helix, the slits are preferably also oriented in a counter-clockwise direction, extending in the counter-clockwise direction from the inner end of the slit at the lumen to the outer end of the slit at the outside sidewall, when viewed from the proximal end. Similarly, if the slits turn in a counter-clockwise direction, the slits are preferably oriented in the clockwise direction, extending in a clockwise direction from the inner end of the slit at the lumen to the outer end of the slit at the outside sidewall. The angling of the slits creates a generally distally directed, tangential flow.

Figure 11:
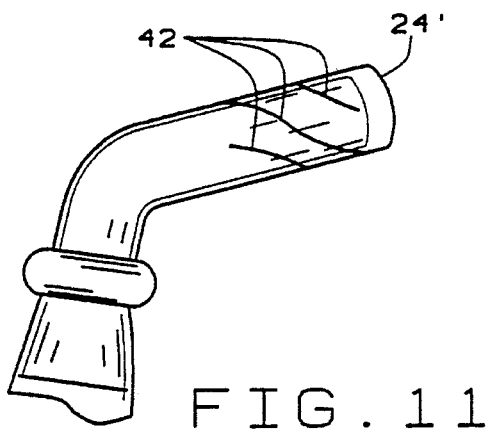
FIG. 11 is a side elevation view of the tip of a second embodiment of an aortic cannula constructed according to the principles of this invention.
Figure 9:
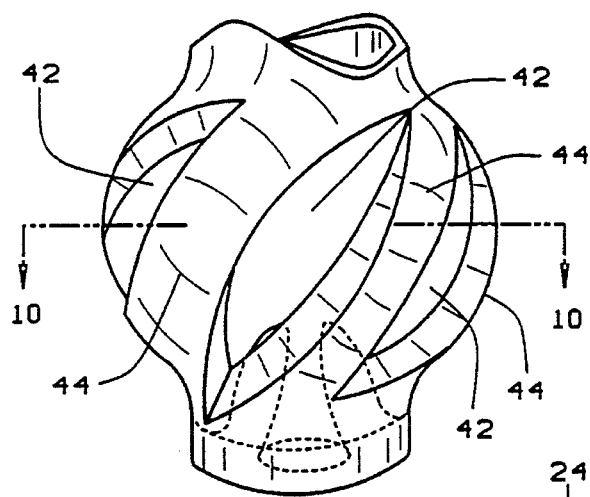
FIG. 9 is a side elevation view of the tip of the first embodiment of the aortic cannula, more completely expanded.
Figure 12:
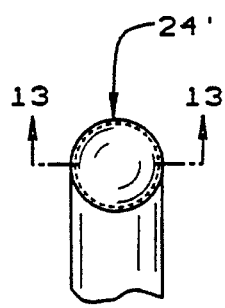
FIG. 12 is an end elevation view of the tip of the second embodiment of the aortic cannula.
Figure 13:
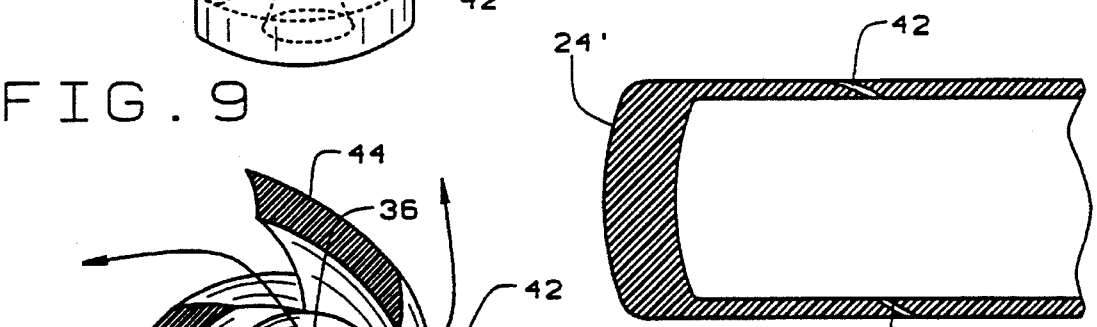
FIG. 13 is a longitudinal cross-sectional view of the tip of the second embodiment of the aortic cannula.
Figure 10:
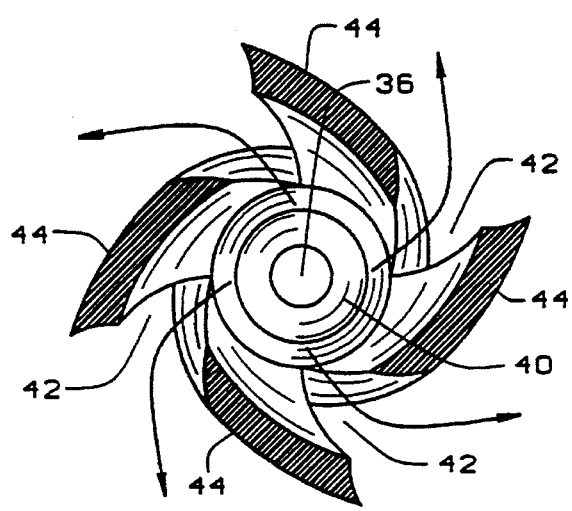
FIG. 10 is a transverse cross sectional view of the tip of the first embodiment of the aortic cannula taken along the plane of line 10—10 in FIG. 9.

The distal end 24 of a second embodiment of an aortic cannula constructed according to the principles of this invention is shown in FIGS. 11–13. The aortic cannula of the second embodiment is identical in construction to the aortic cannula of the first embodiment, except that tip 24' diffuses from tip 24. As shown in FIGS. 11–13, the tip 24 does not have the opening 36 therethrough. As shown in FIGS. 11–13, this distal end also lacks the diffuser 38, although a diffuser inside this lumen could be provided.

This tip 24' has slits 42 which allow fluid to exit the cannula. However, because there are no normally open openings in the distal end, the tip 24' functions as a one-way or check valve. Fluid can exit the tip 24' through slits, which open when the pressure inside the lumen is greater than the pressure surrounding the tip. However, when the pressure inside the lumen is not greater than the pressure surrounding the tip 24', the slits remain closed, blocking flow into the lumen.

OPERATION

In operation, a slit is made in the aorta, and the tip 30 of the cannula is inserted through the slit. The slits 42 make the tip 30 flexible, facilitating the insertion of the tip through the slit in the aorta. Fluid can then be introduced to the aorta through the cannula. As fluid pressure increases inside the cannula the axial component of the pressure acts on the cap 34, tending to slightly elongate the tip 30, which is accommodated by an "unwinding" of the helical struts 44. This "unwinding" which widens the slits 42, thereby increasing the flow through the slits. Because the struts 44 are connected at their proximal and distal ends, this "unwinding" tends to cause the slits 42 to open together, in equal amounts and generally in proportion to the pressure. This achieves an even distribution of flow from the slits, rather than a jetting from fewer than all of the slits. The radial component of the pressure acts to cause the girths of the tip to expand, widening the slits as well. The effective diameter of the expanded cannula is far larger than could have been desirably inserted into the aorta through a slit made therein. Because of the large openings created by the slits, the exit speed and pressure of the blood or other fluid passing through the cannula is reduced over conventional cannulas.

The configuration of the opening through the cap reduces jetting of the fluid that might potentially dislodge atheromatous material from the walls of the aorta. As the fluid pressure increases, the slits 42 open, providing a diffused flow of fluid through the sidewall of the cannula. Because of the large size of the openings formed by the slits, the pressure of the flow is relatively low. The combination of the resilient material from which the tip is made, and the slits 42 automatically accommodate fluctuations in pressure. The slits 42 widen in proportion to the applied pressure, thereby avoiding high pressure build up and high pressure jetting through either the opening 36 or the slits 42.

What is claimed:

1. An improved aortic cannula having a sidewall with a proximal end and a distal end and a lumen therebetween for conducting fluid, the distal end adapted to be inserted into the aorta to deliver fluid to the aorta, the improvement comprising a plurality of helical slits through the sidewall of the distal end of the cannula that widen and narrow proportionally in response to pressure inside the cannula, widening in response to an increase in pressure to reduce fluid exit velocity.

2. The improved aortic cannula according to claim 1 wherein the slits are oriented at an angle with respect to the radial direction.

3. The improved cannula according to claim 2 wherein the slits are oriented in the opposite direction as the helical turn of the slits, when viewed from the proximal to the distal direction.

4. The improved aortic cannula according to claim 2 wherein the helical slits turn clockwise.

5. The improved aortic cannula according to claim 4 wherein the slits are oriented at an angle with respect to the axial direction.

6. The improved cannula according to claim 5 wherein the slits are oriented in a counter-clockwise direction, when viewed from the proximal to the distal direction.

7. The improved aortic cannula according to claim 1 wherein the slits are oriented at an angle with respect to the axial direction.

8. The improved aortic cannula according to claim 1 wherein the slits extend generally outwardly and distally through the wall of the cannula.

9. The improved aortic cannula according to claim 1 wherein there are at least three slits.

10. The improved aortic cannula according to claim 1 wherein there is an opening through the distal end of the cannula.

11. The improved aortic cannula according to claim 10, wherein the opening through the distal end of the cannula widens in the distal direction.

12. The improved aortic cannula according to claim 1 where there is a diffuser inside the lumen for diverting at least a portion of the flow radially outwardly.

13. The improved aortic cannula according to claim 12 wherein the diffuser is generally conical.

14. The improved aortic cannula according to claim 13 wherein there is an opening through the distal end of the cannula, extending generally axially through the conical diffuser.

15. The improved aortic cannula according to claim 14 wherein the opening in the distal end widens in the distal direction.

16. An aortic cannula having a sidewall with a proximal end and a distal end and a lumen therebetween for conducting fluid, the distal end adapted to be inserted into an aorta to deliver fluid to the aorta, the distal end being closed, except for a plurality of helical slits in the sidewall that widen proportionally to the fluid pressure in the lumen to allow fluid to flow outwardly therethrough, when the pressure inside the lumen is greater than that surrounding the distal end, and which close to block flow into the lumen when the pressure inside the lumen is not greater than that surrounding the distal end.

17. A method of delivering fluid to the aorta of a patient comprising the steps of:

making a slit in the aorta of the patient;

inserting the distal end of a cannula into the aorta through the slit, the cannula having a plurality of helical slits through the sidewall of the distal end of the cannula, circumferentially spaced around the distal end of the cannula;

delivering fluid to the cannula sufficient to cause the distal end of the cannula to turn oppositely from the direction of the helical slits, thereby widening the slots to permit the liquid to flow from the distal end of the cannula through the widened slits.

18. A method of delivering fluid to the aorta of a patient comprising the steps of:

making a slit in the aorta of the patient;

inserting the distal end of a cannula into the aorta through the slit, the cannula having a plurality of helical slits through the sidewall of the distal end of the cannula, circumferentially spaced around the distal end of the cannula; and delivering fluid to the cannula sufficient to widen the helical slots to permit the liquid to flow from the distal end of the cannula through the widened slits.

19. An aortic cannula having an inner and outer wall with a proximal and distal end and a lumen therebetween for conducting fluid, the distal end adapted to be inserted into an aorta to deliver fluid to the aorta, the distal end having a plurality of helical slits therein through which fluid can exit the cannula and enter the aorta, the slits having a distal bias extending distally from the inner wall of the cannula to the outer wall of the cannula to impart a distal bias to the fluid that flows through the slits of the cannula.

20. The aortic cannula according to claims 19 wherein the slits have a distal bias such that in longitudinal cross-section the slit extends radially and distally from the inner wall of the cannula to the outer wall of the cannula to impart a distal bias to the fluid that flows through the slits of the cannula.

21. A method of delivering fluid to the aorta of a patient comprising the steps of:

making a slit in the aorta of the patient;

inserting the distal end of a cannula into the aorta through the slit, the cannula having a plurality of helical slits therein which have a distal bias; and delivering fluid to the cannula to create a distally-biased flow from the slits into the aorta.

* * * * *